United States Patent
Jin et al.

(10) Patent No.: US 7,955,823 B2
(45) Date of Patent: Jun. 7, 2011

(54) MICROORGANISM PRODUCING GLUTAMIC ACID IN HIGH YIELD AND A PROCESS OF PRODUCING GLUTAMIC ACID USING THE SAME

(75) Inventors: Chang hyun Jin, Gyeonggi-do (KR); Ki-Hoon Oh, Seoul (KR); Kwang Myung Cho, Gyeonggi-do (KR); Young Hoon Park, Gyeonggi-do (KR)

(73) Assignee: CJ CheilJedang Corporation, Seoul (KR)

( * ) Notice: Subject to any disclaimer, the term of this patent is extended or adjusted under 35 U.S.C. 154(b) by 224 days.

(21) Appl. No.: 12/311,871

(22) PCT Filed: Oct. 11, 2007

(86) PCT No.: PCT/KR2007/004970
§ 371 (c)(1),
(2), (4) Date: Apr. 30, 2009

(87) PCT Pub. No.: WO2008/048017
PCT Pub. Date: Apr. 24, 2008

(65) Prior Publication Data
US 2011/0027840 A1     Feb. 3, 2011

(30) Foreign Application Priority Data
Oct. 16, 2006   (KR) .................. 10-2006-0100448

(51) Int. Cl.
*C12P 13/16* (2006.01)
*C12N 1/20* (2006.01)
(52) U.S. Cl. .................. 435/110; 435/252.32
(58) Field of Classification Search .................. 435/110, 435/252.32
See application file for complete search history.

(56) References Cited

U.S. PATENT DOCUMENTS
2002/0137150 A1   9/2002   Ohtaki et al.
2005/0153402 A1   7/2005   Pompejus et al.

FOREIGN PATENT DOCUMENTS
KR   2000/060972 A   10/2000
WO   01/00844 A2   1/2001

OTHER PUBLICATIONS

"Corynebacterium Glutamicum ATCC 13032, Complete Genome", *NCBI Reference Sequence* NC_006958, Apr. 7, 2005 (pp. 1-2 of 640, excerpt).
J. Kalinowski et al., "The complete *Corynebacterium glutamicum* ATCC 13032 genome sequence and its impact on the production of L-aspartate-derived amino acids and vitamins", *Journal of Biotechnology*, vol. 104, pp. 5-25 (2003).
M. Ikeda et al., "The *Corynebacterium glutamicum* genome: features and impacts on biotechnological processes", *Appl. Microbia Biotechnol.*, vol. 62, pp. 99-109 (2003).
Z. Guo et al., "PcaR-mediated activation and repression of pca genes from *Pseudomonas putida* are propagated by its binding to both the -35 and the -10 promoter elements", Molecular Microbiology, 32(2), pp. 253-263 (1999).
M. Amouyal et al., "Single and Double Loop Formation When deoR Repressor Binds to its Natural Operator Sites", Cell, vol. 58, pp. 545-551 (1989).
C.S. Barbier et al., "Studies on deo operon regulation in *Escherichia coli*; cloning and expression of the cytR structural gene", Gnee, vol. 36, pp. 37-44 (1985).
L. Gaigalat et al., "The DeoR-type transcriptional regulator SugR acts as a repressor for genes encoding the phosphoenolpyruvate:sugar phosphotransferase system (PTS) in *Corynecbacterium glutamicum*", BMC Molecular Biology, 8(104), pp. 1-20 (2007).

*Primary Examiner* — Tekchand Saidha
(74) *Attorney, Agent, or Firm* — Peter F. Corless; Christine C. O'Day; Edwards Angell Palmer & Dodge LLP

(57) ABSTRACT

Disclosed herein are mutant strains, KCCM-10784P and KCCM-10785P, which are obtained through gene manipulation of *Corynebacterium glutamicum* KFCC-11074, and a process of producing L-glutamic acid using the mutant strains. The mutant strains are capable of producing L-Glutamic acid at high yield.

7 Claims, 2 Drawing Sheets

M : 1 kb size marker
Lane 1 ~ 5 : PCR product

M : 1 kb size marker
Lane 1 ~ 3 : PCR product

US 7,955,823 B2

MICROORGANISM PRODUCING GLUTAMIC ACID IN HIGH YIELD AND A PROCESS OF PRODUCING GLUTAMIC ACID USING THE SAME

TECHNICAL FIELD

The present invention relates to a microorganism producing L-glutamic acid at high yield and a process of producing L-glutamic acid using the microorganism. More particularly, the present invention relates to a mutant strain of *Corynebacterium glutamicum* KFCC-11074, which has resistance to kanamycin and/or chloramphenicol and produces L-glutamic acid at high yield, and a process of producing L-glutamic acid using the mutant strain.

BACKGROUND ART

L-glutamic acid is a representative amino acid produced by fermentation. The annual worldwide production of L-glutamic acid is estimated to be more than one million tons, which is comparable to compounds commonly used in the chemical industry. L-glutamic acid has been widely used in pharmaceuticals, food, animal feedstuffs, and other products.

L-glutamic acid has conventionally been produced by fermentation mainly using so-called coryneform L-glutamic acid-producing bacteria belonging to the genus *Brevibacterium, Corynebacterium* or *Microbacterium*, or variants thereof ("Amino Acid Fermentation", Gakkai Shuppan Center, pp. 195-215, 1986). Production of L-glutamic acid by fermentation using other strains includes methods using a microorganism belonging to the genus *Bacillus, Streptomyces* or *Penicillium* (U.S. Pat. No. 3,220,929); a microorganism belonging to the genus *Pseudomonas, Arthrobacter, Serratia* or *Candida* (U.S. Pat. No. 3,563,857); a microorganism such as a bacterium belonging to the genus *Bacillus, Pseudomonas, Serratia*, or *Aerobacter aerogenes* (currently *Enterobacter aerogenes*) (Examined Japanese Patent Publication (KOKOKU) No. 32-9393 (1957)); and a mutant strain of *Escherichia coli* (Japanese Patent Laid-open Application (KOKAI) No. 5-244970 (1993)).

Many studies have been conducted to improve the productivity of L-glutamic acid by changing the medium composition and developing a resistance strain. For example, a strain having resistance to β-fluoropyruvate was developed in order to increase the supply of pyruvate, which is used as an intermediate in the glutamic acid-producing metabolic pathway.

The productivity of L-glutamic acid has been considerably improved through the aforementioned methods. However, to meet increasing demand in the future, a less expensive and more effective process for producing L-glutamic acid needs to be developed.

In this regard, the inventors of this application conducted intensive and thorough research into the development of a bacterial strain producing L-glutamic acid at higher yields. The research resulted in the finding that, when cg2624 and cg2115 genes are knocked out, so that they are not expressed, the knock-out mutant has increased glycerol utilization and produces higher concentrations of L-glutamic acid even with lower biomass compared to a parental strain having an ability to produce L-glutamic acid, thereby leading to the present invention.

DISCLOSURE OF INVENTION

Technical Problem

It is therefore an object of the present invention to provide a mutant strain of *Corynebacterium glutamicum* KFCC-11074, which produces L-glutamic acid at high yield.

It is another object of the present invention to provide a process of preparing the mutant strain.

It is a further object of the present invention to provide a process of producing L-glutamic acid at high yield using the mutant strain.

Technical Solution

In one aspect, the present invention provides a mutant strain of *Corynebacterium glutamicum* KFCC-11074, which is capable of producing L-glutamic acid at high yield.

*Corynebacterium glutamicum* KFCC-11074 is an L-glutamic acid-producing strain, which was obtained prior to the present invention by treating a parental strain, *Corynebacterium glutamicum* KFCC 10656, with a mutagen such as UV irradiation, N-methyl-N'-nitro-N-nitrosoguanidine (NTG), and is capable of growing on a medium containing β-fluoropyruvate. *C. glutamicum* KFCC-11074 is disclosed in Korean Pat. Application No. 1999-09675, the entire disclosure of which is incorporated herein by reference.

A mutant strain of *C. glutamicum* KFCC-11074 according to the present invention is induced by knocking out cg2624 and/or cg2115 genes so that they are not expressed in *C. glutamicum* KFCC-11074. The present inventors intended to utilize glycerol as a carbon source, expecting that glutamic acid productivity can be increased when the carbon source is more effectively utilized and the metabolism thereof via pathways other than glutamic acid synthesis is reduced. In order to confer the ability to utilize glycerol to *C. glutamicum* KFCC-11074, *C. glutamicum* KFCC-11074 was treated with NTG and smeared onto a minimal medium containing glycerol. Among emerged colonies, a rapidly growing colonial population was selected and subjected to DNA array analysis along with the parental strain. The selected single colony exhibited an about 2-fold decrease in expressed levels of cg2624 and cg2115 genes compared to the parental strain. The present inventors expected that, if the KFCC-11074 strain is mutated so as not to express cg2624 and/or cg2115 genes, the strain is able to utilize glycerol as a carbon source and thus may have improved glycerol utilization and increased glutamic acid productivity, and this supposition was confirmed through experiments. Thus, in a preferred aspect, the present invention provides a mutant strain of *C. glutamicum* KFCC-11074, KCCM-10784P, in which the cg2624 gene is not expressed. As well, in a further preferred aspect, the present invention provides a *C. glutamicum* KFCC-11074 mutant strain, KCCM-10785P, in which neither cg2624 nor cg2115 genes are expressed. KCCM-10784P and KCCM-10785 mutant strains were deposited at the Korean Culture Center of Microorganisms (KCCM) on Sep. 28, 2006. The mutant strains according to the present invention were primarily selected on a kanamycin-containing medium because the parental strain KFCC-11074 has resistance to kanamycin. The mutant strain KCCM-10785P (IBT03) further has a chloramphenicol resistance gene.

In another aspect, the present invention provides a process of preparing the mutant strains KCCM-10784P(IBT02) and KCCM-0785P(IBT03).

In a preferred aspect, the mutant strains may be prepared by knocking out the cg2624 gene and/or the cg2115 gene in the parental strain KFCC-11074, which has the ability to produce glutamic acid. Thus, in a detailed aspect, the present invention provides a vector for knocking out the cg2624 gene and/or the cg2115 gene.

As used herein, the term "vector" has commonly known meanings. The term "vector" refers to an extrachromosomal element that may contain a gene, which does not participate in the cellular central metabolism, and is usually a circular double-stranded DNA. The element may be a linear or circular, single-stranded or double-stranded DNA or RNA, which contains a self-replication sequence, a genome integration sequence, or a phage nucleotide sequence. In general, the vector includes sequences suitable for directing gene transcription and translation, a selectable marker, and a sequence directing self-replication or chromosomal integration. A suitable vector contains a 5' region including a transcription initiation site of a gene, and a 3' region for controlling the transcription termination of the gene.

The "suitable regulatory sequence" refers to a sequence capable of controlling the transcription and translation of a polynucleotide (a coding sequence). Examples of such regulatory sequences include a ribosome binding sequence (RBS), a promoter and a terminator. Any promoter capable of initiating the transcription of a gene carried by the vector may be used. Non-limiting examples of such promoters include CYC1, HIS3, GAL1, GAL10, ADH1, PGK, PHO5, GAPDH, ADC1, TRP1, URA3, LEU2, ENO, TPI (useful for expression in *Saccharomyces*), lac, trp, λPL, λPR, T7, tac and trc (useful for expression in *E. coli*). The terminator may be derived from various genes of preferred host cells, or may not be required.

In a preferred aspect, the vector includes a polynucleotide encoding a portion of the cg2624 and/or cg2115 genes of *Corynebacterium glutamicum* in order to knock out cg2624 and/or cg2115 genes. In a preferred embodiment, a polynucleotide containing a partial sequence of the cg2624 gene has the sequence of SEQ ID No. 1, and a polynucleotide containing a partial sequence of the cg2115 gene has the sequence of SEQ ID No. 2. However, it will be apparent to those skilled in the art that the partial sequence of cg2624 and/or cg2115 genes for knockout thereof is not limited to the above sequences, and includes any polynucleotides containing a certain partial sequence of the genes, as long as they are capable of knocking out cg2624 and/or cg2115 genes in the genome of a transformed strain through homologous recombination.

In addition to the partial sequence of cg2624 and/or cg2115 genes, a complete sequence of the genes may be used. In this case, the complete sequence may be partially altered through substitution so as to knock out cg2624 and/or cg2115 genes, leading to the lack of production of a normal translational product thereof. Such a knock-out gene may be constructed using a method known to those skilled in the art.

In an embodiment of the present invention, a vector for knocking out the cg2624 gene was constructed, and included the polynucleotide represented by SEQ ID No. 1. This vector was designated "pCJ200". In an embodiment of the present invention, a knock-out vector for the cg2115 gene was also constructed, and included the polynucleotides of SEQ ID Nos. 2 and 3. The polynucleotide of SEQ ID No. 3 is a nucleotide sequence encoding a cmr gene. The knock-out vector containing the polynucleotides of SEQ ID Nos. 2 and 3 was designated "pCJ201".

When a vector harboring a partial polynucleotide of the cg2624 and/or cg2115 genes is transformed into a *Corynebacterium* species, the polynucleotide carried by the vector is integrated into the host chromosome through homologous recombination so that it knocks out cg2624 and/or cg2115 genes on the host chromosome. Since the vector has a pUC origin, which acts only in *E. coli*, it is unable to replicate in *Corynebacterium* and can replicate only when integrated into the host chromosome. Accordingly, the vector of the present invention may be used to stably integrate the vector itself or an exogenous gene carried by the vector into the chromosome of a microorganism of the genus *Corynebacterium*.

Thus, when the pCJ200 is introduced into a strain, the chromosomal cg2624 gene is knocked out. When the pCJ201 is introduced into a strain, the chromosomal cg2624 and cg2115 genes do not act in the strain, i.e., they are knocked out. The resulting transformed mutant strains do not express mRNA of the genes. In this way, an IBT02 strain, the cg2624 gene of which was disrupted, and an IBT03 strain, the cg2115 and cg2624 genes of which were both disrupted, were obtained and deposited at the Korean Culture Center of Microorganisms (KCCM). The mutant strains displayed decreased OD values and glutamic acid productivity increased by about 20% and about 37%, respectively, compared to a parental strain (see Examples of the present invention).

In a further aspect, the present invention provides a process of producing L-glutamic acid by culturing the mutant strain. In detail, the process comprises knocking out cg2624 and/or cg2115 genes of *C. glutamicum* KFCC-11074 as a parental strain and culturing the gene knock-out strain. In a preferred aspect, the knockout of cg2624 and/or cg2115 genes, as described above, may be induced by introducing a vector containing a partial sequence of the genes into *C. glutamicum* KFCC-11074 to integrate the partial sequence of the cg2624 gene and/or the partial sequence of the cg2115 gene into the KFCC-11074 strain through homologous recombination, preventing the expression of the genes. L-glutamic acid may be produced by culturing the thus-prepared mutant strain in a proper medium.

In a detailed embodiment of the present invention, the vector (pCJ200) containing a partial sequence of the cg2624 gene was transformed into *Corynebacterium*, thereby obtaining an IBT02 strain the cg2624 gene of which was disrupted. The vector (pCJ201), containing a cmr gene and a partial sequences of the cg2115 gene, was transformed into the IBT02 strain, thereby obtaining an IBT03 strain the cg2624 and cg2115 genes of which were both disrupted. The thus obtained KFCC-11704 mutant strains, KFCC-000(IBT02) and KFCC-000(IBT03), were found to have increased glutamic acid productivity compared to the parental strain KFCC-11704 (Table 1).

Advantageous Effects

In accordance with the present invention, a cg2624/cg2115 gene knock-out mutant strain produces glutamic acid at higher yields than a parental strain. Thus, such gene manipulation is useful for increasing the amount of metabolites while controlling the biomass of a microorganism of the genus *Corynebacterium*.

BEST MODE FOR CARRYING OUT THE INVENTION

Figure 1:
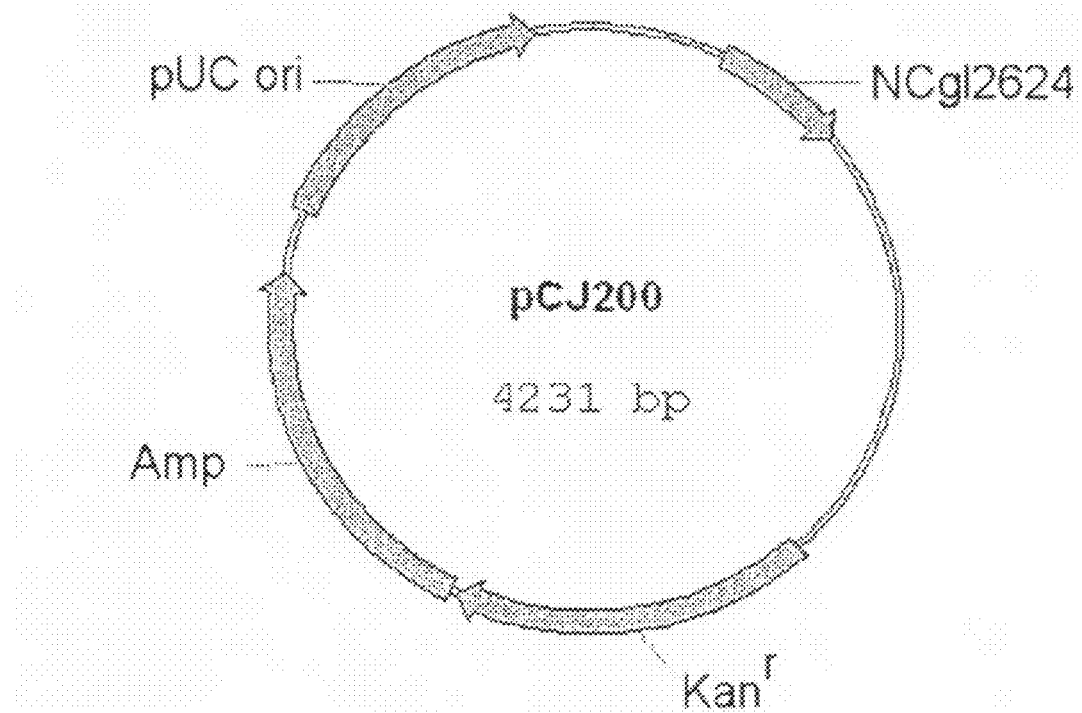
FIG. 1 is a cleavage map of a pCJ200 vector for disrupting the cg2624 gene in *Corynebacterium*.
Figure 2:
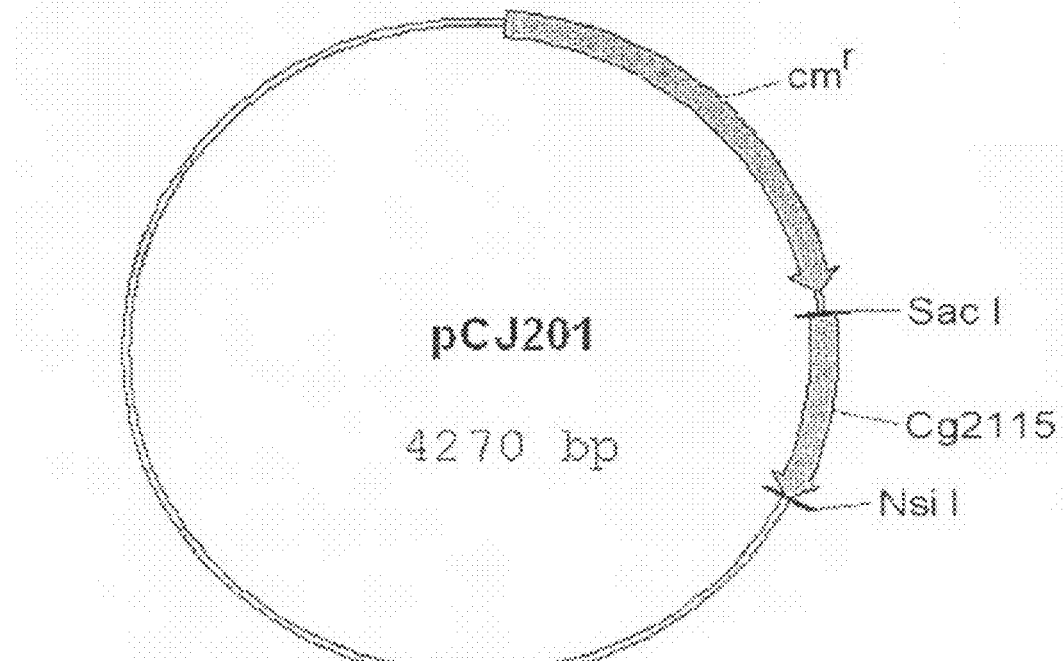
FIG. 2 is a cleavage map of a pCJ201 vector for disrupting the cg2115 gene in *Corynebacterium*.

A better understanding of the present invention may be obtained through the following examples, which are set forth to illustrate, but are not to be construed as the limit of the present invention.

Example 1

Mutagenesis for Selection of Strain Deficient in cg2624 and cg2115 Genes

In order to confer glycerol utilization to a parental strain *C. glutamicum* KFCC-11074, the parental strain was treated with NTG, and smeared onto a minimal medium containing glycerol [10 g/L of glycerol, 5 g/L of ammonium sulfate, 2 g/L of urea, 1 g/L of potassium phosphate monobasic, 2 g/L potassium phosphate dibasic, 0.4 g/L of magnesium sulfate, 0.5 g/L of sodium chloride, 200 µg/L of biotin, 3 mg/L of thiamine, 1 mg/L of pantothenic acid, 5 mg/L of NCA, and 1 ml/L of trace elements (10 mg/L of calcium chloride, 270 mg/L of copper sulfate, 1 g/L of iron chloride, 10 mg/L of manganese chloride, 40 mg/L of ammonium molybdate, 90 mg/L of borax, 10 mg/L of zinc sulfate)]. Among emergent colonies, a colonial population growing rapidly was selected and designated "IBT01". The IBT01 strain was subjected to DNA array analysis along with the parental strain. The IBT01 strain exhibited an about 2-fold decrease in expressed levels of cg2624 and cg2115 genes compared to the parental strain.

Example 2

Cloning of cg2624 Gene

The nucleotide sequence of the cg2624 gene of *Corynebacterium glutamicum* was obtained by searching the nucleotide database at NCBI, and was used to design oligonucleotide primers having the nucleotide sequences of SEQ ID Nos. 6 and 7.

Genomic DNA was extracted from *C. glutamicum*. PCR was carried out using the genomic DNA as a template with the oligonucleotide primers having the nucleotide sequences of SEQ ID Nos. 6 and 7 in order to amplify a partial nucleotide sequence (SEQ ID No. 1) of the cg2624 gene.

The amplified partial nucleotide sequence of the cg2624 gene was cloned into pCR2.1-TOPO (a vector in a TOPO TA Cloning kit) using a TOPO TA Cloning kit (Invitrogen, USA), thereby constructing pCR2.1-TOPO-cg2624(pCJ200).

Example 3

Cloning of cg2115 Gene

The nucleotide sequence of the cg2115 gene of *Corynebacterium glutamicum* was obtained by searching the nucleotide database at NCBI, and was used to design oligonucleotide primers having the nucleotide sequences of SEQ ID Nos. 8 and 9. Genomic DNA was extracted from *C. glutamicum*. PCR was carried out using the genomic DNA as a template with the oligonucleotide primers having the nucleotide sequences of SEQ ID Nos. 8 and 9 in order to amplify the partial nucleotide sequence (SEQ ID No. 2) of the cg2115 gene.

The amplified partial nucleotide sequence of the cg2115 gene was cloned into pCR2.1-TOPO using a TOPO TA Cloning kit (Invitrogen, USA), thereby obtaining pCR2.1-TOPO-cg2115.

Then, the nucleotide sequence of a chloramphenicol resistance gene was obtained by searching the nucleotide database at NCBI, and was used for designing oligonucleotide primers having the nucleotide sequences of SEQ ID Nos. 10 and 11. PCR was carried out using a pACYC-duet vector DNA as a template with the oligonucleotide primers having the nucleotide sequences of SEQ ID Nos. 10 and 11 in order to amplify a chloramphenicol resistance gene (cmr) of the cg2115 gene.

The amplified chloramphenicol resistance gene (cmr) was inserted into a pGEM-T vector (Promega), thereby obtaining pGEM-T-cmr. The pCR2.1-TOPO-cg2115 vector was digested with NsiI and SacI to excise the partial sequence of cg2115 gene, which was purified and ligated with the pGEM-T-cmr vector, predigested with NsiI and SacI, thereby constructing pGEM-T-cmr-cg2115(pCJ201).

Example 4

Transformation of *Corynebacterium* with pCR2.1-Topo-cg2624

*C. glutamicum* KFCC-11074 was cultured in No. 2 medium (10 g/L of polypeptone, 5 g/L of yeast extract, 5 g/L of ammonium sulfate, 1.5 g/L of urea, 4 g/L of potassium phosphate monobasic, 8 g/L of potassium phosphate dibasic, 0.5 g/L of magnesium sulfate, 100 µg/L of biotin, 1 mg/L of thiamine, 2 mg/L of pantothenic acid, 2 mg/L of NCA, 20 g/L of glucose) at 30° C. for 12 hrs. Thereafter, the resulting culture was inoculated into No. 2 EPO medium (No. 2 medium plus 4 g/L of isoniazid, 25 g/L of glycine, 1 g/L of Tween 80) until the culture solution reached an OD value of 0.3, and then cultured at 30° C. until the culture solution reached an OD value of 1.0. Then, the culture was placed on ice for 10 min and centrifuged at 1500×g for 5 min. The cell pellet was washed with 50 ml of pre-cooled 10% glycerol four times, and resuspended in 0.5 ml of 10% glycerol. 100 µl of the cell suspension was transferred into a 1.5-ml micro centrifuge tube.

The pCJ200 vector prepared in Example 1 was added to the competent cells, and transferred into a 2-mm electroporation cuvette on ice. Electroporation was carried out at 1.5 kV, 25 µF and 600Ω. Immediately after electroporation, 1 ml of BHIS medium (37 g/L of brain heart infusion, 91 g/L of sorbitol) was added to the cuvette. The cuvette was incubated at 46° C. for 6 min and then cooled on ice. Then, the cells were smeared onto an active BHIS medium (10 g/L of meat extract, 10 g/L of polypeptone, 5 g/L of yeast extract, 5 g/L of sodium chloride, 18.5 g/L of brain heart infusion, 91 g/L of sorbitol, 20 g/L of agar) supplemented with 25 µg/ml of kanamycin.

Example 5

Evaluation of Integration of the pCJ200 Vector into the Chromosome of *Corynebacterium*

Genomic DNA was isolated from the *Corynebacterium* transformant prepared in Example 4. PCR was carried out using the genomic DNA as a template with a pair of oligonucleotide primers having the nucleotide sequences of SEQ ID Nos. 6 and 7 (M13F and M13R) in order to determine whether the pCJ200 vector was integrated into the host chromosome. PCR products were electrophoresed. A band corresponding to the pCJ200 vector was observed, confirming that the vector was integrated into the host chromosome.

Figure 3:
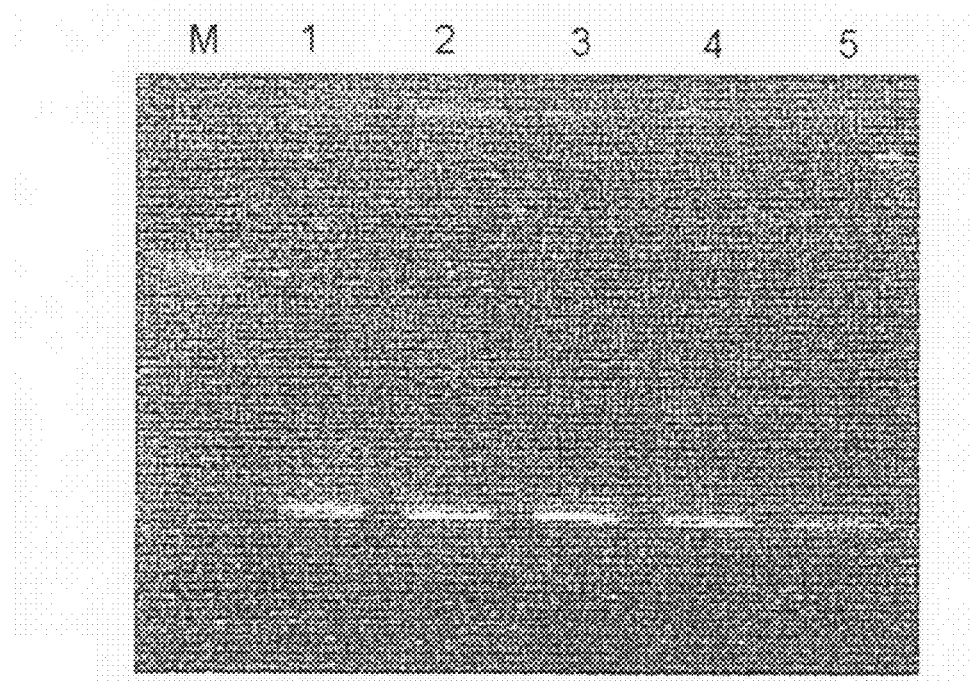
FIG. 3 is a photograph of agarose gel electrophoresis of PCR samples showing that the pCJ200 vector is integrated into the chromosome of *Corynebacterium*.

FIG. 3 is a photograph of agarose gel electrophoresis showing the results of PCR using the genomic DNA, isolated from *Corynebacterium* cells transformed with the pCJ200 vector, as a template with a pair of oligonucleotide primers having nucleotide sequences of SEQ ID Nos. 6 and 7 (M13F and M13R). As shown in FIG. 3, all of five selected clones (lanes 1 to 5) were found to contain the pCJ200 vector within their chromosome. The transformant disrupted in the cg2624 gene through homologous recombination was designated "IBT02" and deposited at the Korean Culture Center of Microorganisms.

Example 6

Transformation of *Corynebacterium* with pCJ201

The transformant IBT02, prepared in Example 5, was further transformed with the pCJ201 vector. The IBT02 strain was transformed according to the same procedure as in Example 4, and smeared onto an active BHIS medium supplemented with 7 μg/ml of chloramphenicol.

Example 7

Evaluation of Integration of the pCJ201 Vector into the Chromosome of *Corynebacterium*

Genomic DNA was isolated from the *Corynebacterium* transformant prepared in Example 6. PCR was carried out, using the genomic DNA as a template, with a pair of oligonucleotide primers having the nucleotide sequences of SEQ ID Nos. 12 and 13 in order to determine whether the pCJ201 vector was integrated into the host chromosome. PCR products were electrophoresed. The oligonucleotides of SEQ ID Nos. 12 and 13 had a partial sequence of the pGEM-T vector.

Figure 4:
FIG. 4 is a photograph of agarose gel electrophoresis of PCR samples showing that the pCJ201 vector is integrated into the chromosome of *Corynebacterium*.

FIG. 4 is a photograph of agarose gel electrophoresis showing the results of PCR using the genomic DNA isolated from *Corynebacterium* cells transformed with the pCJ201 vector, as a template with oligonucleotide primers having nucleotide sequences of SEQ ID Nos. 12 and 13. As shown in FIG. 4, all of three selected clones (lanes 1 to 3) were found to contain the pCJ201 vector within their chromosome. The transformant that was disrupted in both the cg2624 and cg2115 genes was designated "IBT03" and deposited at the KCCM.

Example 8

Evaluation of Glutamic Acid Productivity of the Mutant Strains

The IBT01, IBT02 and IBT03 mutant strains, prepared in Examples 1, 5 and 6, respectively, and the parental strain *C. glutamicum* KFCC-11074 were evaluated for glutamic acid productivity. This test was carried out in a flask. Each strain was grown on an active plate (10 g/L of meat extract, 5 g/L of yeast extract, 10 g/L of polypeptone, 5 g/L of sodium chloride, 20 g/L of agar) at 30° C. for 12 hrs. One loop for each strain was inoculated in a 250-ml flask containing 40 ml of a flask titer medium (3% glucose, 1% molasses, 0.04% magnesium sulfate, 0.1% potassium phosphate dibasic, 0.3% ammonium sulfate, 0.001% iron sulfate, 0.001% manganese sulfate, 500 μg/L biotin, 2 mg/L thiamine hydrochloride, 0.1% urea, pH 7.1), and was grown at 30° C. for 40 hrs. The culture was evaluated for glutamic acid productivity. As shown in Table 1, the IBT01 strain displayed a decreased OD value and an increased glutamic acid yield compared to the parental strain. Also, the IBT02 and IBT03 strains displayed a decreased OD value and glutamic acid yields increased by 20% and 37%, respectively, compared to the parental strain. These results indicate that the IBT02 and IBT03 mutant strains produce L-glutamic acid at higher yields than the parental strain.

TABLE 1

| | Glutamic Acid Productivity | | | |
| --- | --- | --- | --- | --- |
| | 24 h | | 40 h | |
| Strains | OD | GA (g/L) | OD | GA (g/L) |
| KFCC-11074 | 18.8 | 10.2 | 20.8 | 11.5 |
| IBT01 | 12.2 | 9.1 | 15.4 | 11.9 |
| IBT02 | 12.2 | 9.5 | 13.5 | 13.7 |
| IBT03 | 5.8 | 8.4 | 8.1 | 15.8 |

The invention claimed is:

1. A mutant strain of *Corynebacterium glutamicum* KFCC-11074, in which cg2624 gene is knocked out and which produces L-glutamic acid in high yields.

2. A mutant strain of *Corynebacterium glutamicum* KFCC-11074, in which both cg2624 and cg2115 genes are knocked out and which produces L-glutamic acid in high yields.

3. The mutant strain according to claim 1, which is *Corynebacterium glutamicum*, in which the cg2624 gene is not expressed.

4. The mutant strain according to claim 2, which is *Corynebacterium glutamicum*, in which the cg2624 and cg2115 genes are not expressed.

5. The mutant strain according to claim 2, which has resistance to chloramphenicol.

6. A method of producing a mutant strain having increased glycerol utilization and producing L-glutamic acid in high yields, comprising knocking out cg2624 gene and/or cg2115 gene of *Corynebacterium glutamicum* KFCC-11074.

7. A method of producing L-glutamic acid in high yields by culturing the mutant strain of any one of claims 1 to 5.

* * * * *

SEQUENCE LISTING

```
<160> NUMBER OF SEQ ID NOS: 13

<210> SEQ ID NO 1
<211> LENGTH: 314
<212> TYPE: DNA
<213> ORGANISM: Corynebacterium glutamicum

<400> SEQUENCE: 1
cgccagattt cgtacaatca tttgcccgcg gcttatctgt gatccgaagt ttcagcgcag      60
ataatccatc gcaaacactg tccgaagtcg ccagccaaac tggactctca agggccaccg     120
ctaggcgctt tctccacacc ttgaccgacc ttggatatgc ggtaaacaac gattcccggt     180
tccagctcac accacgtgtt ttggagcttg gagcaagcta cctttccgca ttgtccctgc     240
ctgcgatcgc gcagccccgc ctggaggtac tctcccgcca ggtcggcgaa tcaagctcca     300
tgtccgtact cgac                                                       314

<210> SEQ ID NO 2
<211> LENGTH: 300
<212> TYPE: DNA
```

<213> ORGANISM: Corynebacterium glucuronolyticum

<400> SEQUENCE: 2

| | | | | | |
|---|---|---|---|---|---|
| ccgtcgacag | attgcctcat | taacggcagt | tgagggacgt | gtaaatgtca | cagaattagc | 60 |
| gggccgattc | gatgtcactg | cagagacgat | tcgacgagac | cttgcggtgc | tagaccgcga | 120 |
| gggaattgtt | caccgcgttc | acggtggcgc | agtagccacc | caatctttcc | aaaccacaga | 180 |
| gttgagcttg | gatactcgtt | tcaggtctgc | atcgtcagca | agtactcca | ttgccaaggc | 240 |
| agcgatgcag | ttcctgcccg | ctgagcatgg | cggactgttc | ctcgatgcgg | gaactactgt | 300 |

<210> SEQ ID NO 3
<211> LENGTH: 893
<212> TYPE: DNA
<213> ORGANISM: Corynebacterium glutamicum

<400> SEQUENCE: 3

| | | | | | |
|---|---|---|---|---|---|
| cgtttaaggg | caccaataac | tgccttaaaa | aaattacgcc | ccgccctgcc | actcatcgca | 60 |
| gtactgttgt | aattcattaa | gcattctgcc | gacatggaag | ccatcacaaa | cggcatgatg | 120 |
| aacctgaatc | gccagcggca | tcagcacctt | gtcgccttgc | gtataatatt | tgcccatggt | 180 |
| gaaaacgggg | gcgaagaagt | tgtccatatt | ggccacgttt | aaatcaaaac | tggtgaaact | 240 |
| cacccaggga | ttggctgaga | cgaaaaacat | attctcaata | aacccttag | ggaaataggc | 300 |
| caggttttca | ccgtaacacg | ccacatcttg | cgaatatatg | tgtagaaact | gccggaaatc | 360 |
| gtcgtggtat | tcactccaga | gcgatgaaaa | cgtttcagtt | tgctcatgga | aaacggtgta | 420 |
| acaagggtga | acactatccc | atatcaccag | ctcaccgtct | ttcattgcca | tacggaattc | 480 |
| cggatgagca | ttcatcaggc | gggcaagaat | gtgaataaag | gccggataaa | acttgtgctt | 540 |
| atttttcttt | acggtcttta | aaaggccgt | aatatccagc | tgaacggtct | ggttataggt | 600 |
| acattgagca | actgactgaa | atgcctcaaa | atgttcttta | cgatgccatt | gggatatatc | 660 |
| aacggtggta | tatccagtga | ttttttctc | cattttagct | tccttagctc | ctgaaaatct | 720 |
| cgataactca | aaaatacgc | ccggtagtga | tcttatttca | ttatggtgaa | agttggaacc | 780 |
| tcttacgtgc | cgatcaacgt | ctcatttccg | ccaaaagttg | gccagggct | tcccggtatc | 840 |
| aacagggaca | ccaggattta | tttattctgc | gaagtgatct | tccgtcacag | gta | 893 |

<210> SEQ ID NO 4
<211> LENGTH: 4245
<212> TYPE: DNA
<213> ORGANISM: Corynebacterium glutamicum

<400> SEQUENCE: 4

| | | | | | |
|---|---|---|---|---|---|
| agcgcccaat | acgcaaaccg | cctctccccg | cgcgttggcc | gattcattaa | tgcagctggc | 60 |
| acgacaggtt | tcccgactgg | aaagcgggca | gtgagcgcaa | cgcaattaat | gtgagttagc | 120 |
| tcactcatta | ggcaccccag | gctttacact | ttatgcttcc | ggctcgtatg | ttgtgtggaa | 180 |
| ttgtgagcgg | ataacaattt | cacacaggaa | acagctatga | ccatgattac | gccaagcttg | 240 |
| gtaccgagct | cggatccact | agtaacggcc | gccagtgtgc | tggaattcgc | ccttcgccag | 300 |
| atttcgtaca | atcatttgcc | cgcggcttat | ctgtgatccg | aagtttcagc | gcagataatc | 360 |
| catcgcaaac | actgtccgaa | gtcgccagcc | aaactggact | ctcaagggcc | accgctaggc | 420 |
| gctttctcca | caccttgacc | gaccttggat | atgcggtaaa | caacgattcc | cggttccagc | 480 |
| tcacaccacg | tgttttggag | cttggagcaa | gctacctttc | gcattgtccc | tgcctgcga | 540 |
| tcgcgcagcc | ccgcctggag | gtactctccc | gccaggtcgg | cgaatcaagc | tccatgtccg | 600 |

```
tactcgacaa gggcgaattc tgcagatatc catcacactg gcggccgctc gagcatgcat    660
ctagagggcc caattcgccc tatagtgagt cgtattacaa ttcactggcc gtcgttttac    720
aacgtcgtga ctgggaaaac cctggcgtta cccaacttaa tcgccttgca gcacatcccc    780
ctttcgccag ctggcgtaat agcgaagagg cccgcaccga tcgcccttcc caacagttgc    840
gcagcctgaa tggcgaatgg acgcgccctg tagcggcgca ttaagcgcgg cgggtgtggt    900
ggttacgcgc agcgtgaccg ctacacttgc cagcgcccta gcgcccgctc ctttcgcttt    960
cttcccttcc tttctcgcca cgttcgccgg ctttccccgt caagctctaa atcgggggct   1020
ccctttaggg ttccgattta gtgctttacg gcacctcgac cccaaaaaac ttgattaggg   1080
tgatggttca cgtagtgggc catcgccctg atagacggtt tttcgccctt gacgttgga    1140 gtccacgttc tttaatagtg gactcttgtt ccaaactgga acaacactca accctatctc   1200
ggtctattct tttgatttat aagggatttt gccgatttcg gcctattggt taaaaatga    1260 gctgatttaa caaaaattta cgcgaatttt aacaaaatt cagggcgcaa gggctgctaa    1320
aggaagcgga acacgtagaa agccagtccg cagaaacggt gctgaccccg gatgaatgtc   1380
agctactggg ctatctggac aagggaaaac gcaagcgcaa agagaaagca ggtagcttgc   1440
agtgggctta catggcgata gctagactgg gcggttttat ggacagcaag cgaaccggaa   1500
ttgccagctg gggcgccctc tggtaaggtt gggaagccct gcaaagtaaa ctggatggct   1560
ttcttgccgc caaggatctg atggcgcagg ggatcaagat ctgatcaaga acaggatga    1620 ggatcgtttc gcatgattga acaagatgga ttgcacgcag gttctccggc cgcttgggtg   1680
gagaggctat tcggctatga ctgggcacaa cagacaatcg gctgctctga tgccgccgtg   1740
ttccggctgt cagcgcaggg gcgcccggtt ctttttgtca agaccgacct gtccggtgcc   1800
ctgaatgaac tgcaggacga ggcagcgcgg ctatcgtggc tggccacgac gggcgttcct   1860
tgcgcagctg tgctcgacgt tgtcactgaa gcgggaaggg actggctgct attgggcgaa   1920
gtgccggggc aggatctcct gtcatcccac cttgctcctg ccgagaaagt atccatcatg   1980
gctgatgcaa tgcggcggct gcatacgctt gatccggcta cctgcccatt cgaccaccaa   2040
gcgaaacatc gcatcgagcg agcacgtact cggatggaag ccggtcttgt cgatcaggat   2100
gatctggacg aagagcatca ggggctcgcg ccagccgaac tgttcgccag gctcaaggcg   2160
cgcatgcccg acggcgagga tctcgtcgtg acccatggcg atgcctgctt gccgaatatc   2220
atggtggaaa atggccgctt ttctggattc atcgactgtg gccggctggg tgtggcggac   2280
cgctatcagg acatagcgtt ggctacccgt gatattgctg aagagcttgg cggcgaatgg   2340
gctgaccgct tcctcgtgct ttacggtatc gccgctcccg attcgcagcg catcgccttc   2400
tatcgccttc ttgacgagtt cttctgaatt gaaaaggaa gagtatgagt attcaacatt   2460
tccgtgtcgc ccttattccc ttttttgcgg cattttgcct tcctgttttt gctcacccag   2520
aaacgctggt gaaagtaaaa gatgctgaag atcagttggg tgcacgagtg ggttacatcg   2580
aactggatct caacagcggt aagatccttg agagttttcg ccccgaagaa cgttttccaa   2640
tgatgagcac ttttaaagtt ctgctatgtg gcgcggtatt atcccgtatt gacgccgggc   2700
aagagcaact cggtcgccgc atacactatt ctcagaatga cttggttgag tactcaccag   2760
tcacagaaaa gcatcttacg gatggcatga cagtaagaga attatgcagt gctgccataa   2820
ccatgagtga taacactgcg gccaacttac ttctgacaac gatcggagga ccgaaggagc   2880
taaccgcttt tttgcacaac atgggggatc atgtaactcg ccttgatcgt tgggaaccgg   2940
agctgaatga agccatacca aacgacgagc gtgacaccac gatgcctgta gcaatggcaa   3000
```

```
caacgttgcg caaactatta actggcgaac tacttactct agcttcccgg caacaattaa    3060
tagactggat ggaggcggat aaagttgcag gaccacttct gcgctcggcc cttccggctg    3120
gctggtttat tgctgataaa tctggagccg gtgagcgtgg gtctcgcggt atcattgcag    3180
cactggggcc agatggtaag ccctcccgta tcgtagttat ctacacgacg gggagtcagg    3240
caactatgga tgaacgaaat agacagatcg ctgagatagg tgcctcactg attaagcatt    3300
ggtaactgtc agaccaagtt tactcatata ctttagat tgatttaaaa cttcattttt     3360
aatttaaaag gatctaggtg aagatccttt ttgataatct catgaccaaa atcccttaac    3420
gtgagttttc gttccactga gcgtcagacc ccgtagaaaa gatcaaagga tcttcttgag    3480 atccttttttt tctgcgcgta atctgctgct tgcaaacaaa aaaaccaccg ctaccagcgg    3540
tggtttgttt gccggatcaa gagctaccaa ctcttttttcc gaaggtaact ggcttcagca    3600
gagcgcagat accaaatact gttcttctag tgtagccgta gttaggccac cacttcaaga    3660
actctgtagc accgcctaca tacctcgctc tgctaatcct gttaccagtg gctgctgcca    3720
gtggcgataa gtcgtgtctt accgggttgg actcaagacg atagttaccg gataaggcgc    3780
agcggtcggg ctgaacgggg ggttcgtgca cacagcccag cttggagcga acgacctaca    3840
ccgaactgag atacctacag cgtgagctat gagaaagcgc cacgcttccc gaagggagaa    3900
aggcggacag gtatccggta agcggcaggg tcggaacagg agagcgcacg agggagcttc    3960 caggggggaaa cgcctggtat ctttatagtc ctgtcgggtt tcgccacctc tgacttgagc    4020
gtcgattttt gtgatgctcg tcagggggggc ggagcctatg gaaaaacgcc agcaacgcgg    4080
cctttttacg gttcctggcc ttttgctggc cttttgctca catgttcttt cctgcgttat    4140
cccctgattc tgtggataac cgtattaccg cctttgagtg agctgatacc gctcgccgca    4200
gccgaacgac cgagcgcagc gagtcagtga gcgaggaagc ggaag                    4245
```

<210> SEQ ID NO 5
<211> LENGTH: 4270
<212> TYPE: DNA
<213> ORGANISM: Artificial Sequence
<220> FEATURE:
<223> OTHER INFORMATION: Description of Artificial Sequence: Synthetic
      Polynucleotide sequence of pCJ201 vector

<400> SEQUENCE: 5

```
gggcgaattg ggcccgacgt cgcatgctcc cggccgccat ggccgcggga tcgtttaagg     60
gcaccaataa ctgccttaaa aaaattacgc cccgccctgc cactcatcgc agtactgttg    120
taattcatta agcattctgc cgacatggaa gccatcacaa acggcatgat gaacctgaat    180
cgccagcggc atcagcacct gtcgccttg cgtataatat ttgcccatgg tgaaaacggg    240
ggcgaagaag ttgtccatat tggccacgtt taaatcaaaa ctggtgaaac tcacccaggg    300
attggctgag acgaaaaaca tattctcaat aaacccttta gggaaatagg ccaggttttc    360
accgtaacac gccacatctt gcgaatatat gtgtagaaac tgccgaaat cgtcgtggta     420 ttcactccag agcgatgaaa acgtttcagt ttgctcatgg aaaacggtgt aacaagggtg    480
aacactatcc catatcacca gctcaccgtc tttcattgcc atacggaatt ccggatgagc    540
attcatcagg cgggcaagaa tgtgaataaa ggccggataa aacttgtgct tatttttctt    600
tacggtcttt aaaaaggccg taatatccag ctgaacggtc tggttatagg tacattgagc    660
aactgactga aatgcctcaa aatgttcttt acgatgccat gggatatat caacggtggt     720 atatccagtg atttttttct ccattttagc ttccttagct cctgaaaatc tcgataactc    780
aaaaaatacg cccggtagtg atcttatttc attatggtga aagttggaac ctcttacgtg    840
```

```
ccgatcaacg tctcattttc gccaaaagtt ggcccagggc ttcccggtat caacagggac    900
accaggattt atttattctg cgaagtgatc ttccgtcaca ggtaatcact agtgcggccg    960
cctgcaggtc gaccatatgg gagagctcgg atccactagt aacggccgcc agtgtgctgg   1020
aattcgccct tccgtcgaca gattgcctca ttaacggcag ttgagggacg tgtaaatgtc   1080
acagaattag cgggccgatt cgatgtcact gcagagacga ttcgacgaga ccttgcggtg   1140
ctagaccgcg agggaattgt tcaccgcgtt cacggtggcg cagtagccac ccaatctttc   1200
caaaccacag agttgagctt ggatactcgt ttcaggtctg catcgtcagc aaagtactcc   1260
attgccaagg cagcgatgca gttcctgccc gctgagcatg gcggactgtt cctcgatgcg   1320
ggaactactg taagggcgaa ttctgcagat atccatcaca ctggcggccg ctcgagcatg   1380
catagcttga gtattctata gtgtcaccta aatagcttgg cgtaatcatg gtcatagctg   1440
tttcctgtgt gaaattgtta tccgctcaca attccacaca acatacgagc cggaagcata   1500
aagtgtaaag cctggggtgc ctaatgagtg agctaactca cattaattgc gttgcgctca   1560
ctgcccgctt tccagtcggg aaacctgtcg tgccagctgc attaatgaat cggccaacgc   1620
gcggggagag gcggtttgcg tattgggcgc tcttccgctt cctcgctcac tgactcgctg   1680
cgctcggtcg ttcggctgcg gcgagcggta tcagctcact caaaggcggt aatacggtta   1740
tccacagaat caggggataa cgcaggaaag aacatgtgag caaaaggcca gcaaaaggcc   1800
aggaaccgta aaaaggccgc gttgctggcg ttttttccata ggctccgccc cctgacgag   1860
catcacaaaa atcgacgctc aagtcagagg tggcgaaacc cgacaggact ataaagatac   1920
caggcgtttc cccctggaag ctccctcgtg cgctctcctg ttccgaccct gccgcttacc   1980
ggatacctgt ccgcctttct cccttcggga agcgtggcgc tttctcatag ctcacgctgt   2040
aggtatctca gttcggtgta ggtcgttcgc tccaagctgg gctgtgtgca cgaaccccc   2100
gttcagcccg accgctgcgc cttatccggt aactatcgtc ttgagtccaa cccggtaaga   2160
cacgacttat cgccactggc agcagccact ggtaacagga ttagcagagc gaggtatgta   2220
ggcggtgcta cagagttctt gaagtggtgg cctaactacg gctacactag aagaacagta   2280
tttggtatct gcgctctgct gaagccagtt accttcggaa aaagagttgg tagctcttga   2340
tccggcaaac aaaccaccgc tggtagcggt ggtttttttg tttgcaagca gcagattacg   2400
cgcagaaaaa aaggatctca agaagatcct ttgatctttt ctacggggtc tgacgctcag   2460
tggaacgaaa actcacgtta agggattttg gtcatgagat tatcaaaaag gatcttcacc   2520
tagatccttt taaattaaaa atgaagtttt aaatcaatct aaagtatata tgagtaaact   2580
tggtctgaca gttaccaatg cttaatcagt gaggcaccta tctcagcgat ctgtctattt   2640
cgttcatcca tagttgcctg actccccgtc gtgtagataa ctacgatacg ggagggctta   2700
ccatctggcc ccagtgctgc aatgataccg cgagacccac gctcaccggc tccagattta   2760
tcagcaataa accagccagc cggaagggcc gagcgcagaa gtggtcctgc aactttatcc   2820
gcctccatcc agtctattaa ttgttgccgg gaagctagag taagtagttc gccagttaat   2880
agtttgcgca acgttgttgc cattgctaca ggcatcgtgg tgtcacgctc gtcgtttggt   2940
atggcttcat tcagctccgg ttcccaacga tcaaggcgag ttacatgatc ccccatgttg   3000
tgcaaaaaag cggttagctc cttcggtcct ccgatcgttg tcagaagtaa gttggccgca   3060
gtgttatcac tcatggttat ggcagcactg cataattctc ttactgtcat gccatccgta   3120
agatgctttt ctgtgactgg tgagtactca accaagtcat tctgagaata gtgtatgcgg   3180
cgaccgagtt gctcttgccc ggcgtcaata cgggataata ccgcgccaca tagcagaact   3240
```

```
ttaaaagtgc tcatcattgg aaaacgttct tcggggcgaa aactctcaag gatcttaccg    3300
ctgttgagat ccagttcgat gtaacccact cgtgcaccca actgatcttc agcatctttt    3360
actttcacca gcgtttctgg gtgagcaaaa acaggaaggc aaaatgccgc aaaaaaggga    3420
ataagggcga cacggaaatg ttgaatactc atactcttcc ttttttcaata ttattgaagc    3480 atttatcagg gttattgtct catgagcgga tacatatttg aatgtatttta gaaaaataaa    3540 caaatagggg ttccgcgcac atttccccga aaagtgccac ctgatgcggt gtgaaatacc    3600
gcacagatgc gtaaggagaa ataccgcat caggaaattg taagcgttaa tattttgtta    3660
aaattcgcgt taaattttg ttaaatcagc tcatttttta accaataggc cgaaatcggc    3720 aaaatcccctt ataaatcaaa agaatagacc gagataggt tgagtgttgt tccagtttgg    3780
aacaagagtc cactattaaa gaacgtggac tccaacgtca aagggcgaaa aaccgtctat    3840
cagggcgatg gcccactacg tgaaccatca ccctaatcaa gttttttggg gtcgaggtgc    3900
cgtaaagcac taaatcggaa ccctaaaggg agcccccgat ttagagcttg acggggaaag    3960
ccggcgaacg tggcgagaaa ggaagggaag aaagcgaaag gagcgggcgc tagggcgctg    4020
gcaagtgtag cggtcacgct gcgcgtaacc accacaccg ccgcgcttaa tgcgccgcta    4080
cagggcgcgt ccattcgcca ttcaggctgc gcaactgttg ggaagggcga tcggtgcggg    4140
cctcttcgct attacgccag ctggcgaaag ggggatgtgc tgcaaggcga ttaagttggg    4200
taacgccagg gttttcccag tcacgacgtt gtaaaacgac ggccagtgaa ttgtaatacg    4260
actcactata                                                          4270

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer for cg2624 amplification from Corynebacterium
      glutamicumi

<400> SEQUENCE: 6
cgccagattt cgtacaatca t                                             21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer for cg2624 amplification from Corynebacterium
      glutamicumi

<400> SEQUENCE: 7
gtcgagtacg gacatggagc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer for cg2115 amplification from Corynebacterium
      glutamicumi

<400> SEQUENCE: 8
ccgtcgacag attgcctcat                                               20
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer for cg2115 amplification from Corynebacterium
      glutamicumi

<400> SEQUENCE: 9
acagtagttc ccgcatcgag                                              20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      forward primer for cg2115 amplification from chloramphenicol
      resistant gene

<400> SEQUENCE: 10
cgtttaaggg caccaataa                                               19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer for cg2115 amplification from chloramphenicol
      resistant gene

<400> SEQUENCE: 11
tacctgtgac ggaagatcac t                                            21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for conformation of cg2115 knock out

<400> SEQUENCE: 12
taatacgact cactataggg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for conformation of cg2115 knock out

<400> SEQUENCE: 13
atttaggtga cactatagaa                                              20
```